United States Patent [19]

Kimura et al.

[11] Patent Number: 5,929,221
[45] Date of Patent: Jul. 27, 1999

[54] GENE DERIVED FROM CORYNEFORM BACTERIA AND USE THEREOF

[75] Inventors: Eiichiro Kimura; Chizu Abe; Yoshio Kawahara; Yasuhiko Yoshihara; Tsuyoshi Nakamatsu, all of Kawasaki, Japan

[73] Assignee: Ajinomoto Co., Inc., Tokyo, Japan

[21] Appl. No.: 08/693,228

[22] PCT Filed: Feb. 23, 1995

[86] PCT No.: PCT/JP95/00269

§ 371 Date: Aug. 22, 1996

§ 102(e) Date: Aug. 22, 1996

[87] PCT Pub. No.: WO95/23224

PCT Pub. Date: Aug. 31, 1995

[30] Foreign Application Priority Data

Feb. 24, 1994 [JP] Japan ................................... 6-026501

[51] Int. Cl.⁶ .................. C07H 21/02; C07H 21/04; C12Q 1/68; C12N 15/00
[52] U.S. Cl. .............................. 536/23.1; 536/24.3; 435/6; 935/76; 935/77; 935/78
[58] Field of Search ................................. 435/106, 6, 110, 435/115, 253.32, 253.3; 935/76–78; 536/24.3, 23.1

[56] References Cited

U.S. PATENT DOCUMENTS

| 3,929,571 | 12/1975 | Kubota et al. | 195/29 |
| 3,971,701 | 7/1976 | Takinami et al. | 195/47 |
| 4,514,502 | 4/1985 | Miwa et al. | 435/253 |
| 4,757,009 | 7/1988 | Sano et al. | 435/106 |
| 4,861,722 | 8/1989 | Sano et al. | 435/252.32 |
| 4,968,609 | 11/1990 | Ito et al. | 435/108 |
| 4,980,285 | 12/1990 | Sano et al. | 435/108 |
| 5,128,451 | 7/1992 | Allen | 530/350 |
| 5,326,693 | 7/1994 | Kuronuma et al. | 435/42 |
| 5,426,050 | 6/1995 | Morinaga et al. | 435/252.32 |
| 5,498,532 | 3/1996 | Katsumata et al. | 435/106 |
| 5,516,660 | 5/1996 | Wagner et al. | 435/106 |
| 5,597,727 | 1/1997 | Kohama et al. | 435/252.32 |

FOREIGN PATENT DOCUMENTS

| 0 469 517 A2 | 2/1992 | European Pat. Off. . |
| 2 230 723 | 12/1974 | France . |
| 57-115186 | 7/1982 | Japan . |
| 1 106 554 | 3/1968 | United Kingdom . |

OTHER PUBLICATIONS

Journal of Antimicrobial Chemotherapy, vol. 14, pp. 115–124, 1984, D.E. Townsend, et al., "Transposition of Gentamicin Resistance to Staphylococcal Plasmids Encoding Resistance to Cationic Agents".

Database WPI, Derwent Publications, AN–66–39927F, JP–A–44–021392, Sep. 12, 1969.

Soubrier et al., Gene 116:99–104 (1992).

Finegold Et al., "Diagnostic Microbiology", pp.291–297, 6th Edition, published by C.V. Mosby Co. St.Louis, MO (1982).

Singleton et al., "Dictionary of Microbiology and Molecular Biology", pp.229–230, published by John Wiley & Sons Ltd, Great Britain (1987).

The ATCC Catalog, 18th Edition, pp. 66–69 and 92–108 (1992).

Kraus et al., PNAS 83:8049–8053 (1986).

Bernard et al., J. of Clinical Microbiology 32(5):1217–1222 (May 1994).

Funke et al., J. of Clinical Microbiology 32(5):1223–1228 (May 1994).

Lamhonwah et al., PNAS 83:4864–4868 (1986).

Ajinomoto, JP 5–3793, abstract only (Jan. 14, 1993).

Ajinomoto, JP 52–24593, absrtract only (May 31, 1975).

AsaHi Chem IND CO. LTD, WPI/ Derwent 66–39927F, abstract only (Sep. 12, 1969).

Townsend et al., J. of Antimicrobial Chenmotheraopy 14:115–124 (1984).

*Primary Examiner*—W. Gary Jones
*Assistant Examiner*—Ethan Whisenant
*Attorney, Agent, or Firm*—Oblon, Spivak, McClelland, Maier & Neustadt, P.C.

[57] ABSTRACT

The L-lysine productivity of an L-lysine producing Coryneform bacterium is enhanced by amplifying a novel gene derived from a Coryneform bacterium and participating in L-glutamic acid production, while the L-glutamic acid productivity of an L-glutamic acid-producing Coryneform bacterium is enhanced by suppressing the function of the gene.

17 Claims, 2 Drawing Sheets

GENE DERIVED FROM CORYNEFORM BACTERIA AND USE THEREOF

This application is a 371 of PCT/JP95/00269 filed Feb. 23, 1995.

FIELD OF THE INVENTION

The present invention relates to breeding and use of Coryneform bacteria which are used for the fermentative production of L-amino acids such as L-glutamic acid and L-lysine and other substances, and the use thereof.

DESCRIPTION OF THE PRIOR ART

When Coryneform bacteria are cultivated in a medium having a limited amount of biotin, they produce a large amount of L-glutamic acid. On the other hand, when the Coryneform bacteria are cultivated in a medium containing an excess amount of biotin, they do not produce L-glutamic acid. However, it is known that if a surfactant or penicillin is added to a medium containing such an excess amount of biotin, the growth of the bacteria in this medium is inhibited and the bacteria produce a large amount of L-glutamic acid therein.

To make Coryneform bacteria produce L-glutamic acid, any of the following means is effective.

1. The biotin concentration in the medium is made suboptimal. Refer to S. Okumura, T. Tsugawa, T. Tsunoda and A. Kitai, Nippon Nogeikagaku Kaishi, 36, 197–203 (1962).

2. A surfactant is added to the medium provided that a sufficient amount of biotin is present. Refer to I. Shiio, H. Otsuka and N. Atsuya, J. Biochem., 53, 333–340 (1963); K. Takinami, H. Okada and T. Tsunoda, Agr. Biol. Chem., 27, 853–863 (1963).

3. Penicillin is added to the medium provided that a sufficient amount of biotin is present. Refer to U.S. Pat. No. 3,080,297; Japanese Patent Publication No. 37-1695 (1962); M. Shibui, T. Kurima, S. Okabe and T. Osawa, Amino Acid and Nucleic Acid, 17, 61–65 (1968).

The mechanisms in these means have been considered in the following way.

With respect to L-glutamic acid production by limitation of biotin, the major factor is considered as follows: Biotin is a coenzyme for acetyl-CoA carboxylase for the synthesis of fatty acids and, in addition, unsaturated fatty acids, such as oleic acid, and their derivatives have a substitutive effect for biotin. Therefore, biotin will have an influence on the composition of fatty acids constituting the cell membrane, thereby varying the permeability of L-glutamic acid through the cell membrane (I. Shiio, S. Otsuka and M. Takahashi, J. Biochem., 51, 56–62 (1962); I. Shiio, K. Narui, N. Yahaba and M. Takahashi, J. Biochem., 51, 109–111 (1962)).

The production of L-glutamic acid by addition of a surfactant or penicillin has also been considered with reference to the variation in the permeability of L-glutamic acid through the cytoplasmic membrane because of the variation in the structure of cell surface (Shiio, S. Otsuka and N, Katsuya, J. Biochem., 53, 333–340 (1963)).

As mentioned above, the production of L-glutamic acid has been discussed with reference to its permeability through cell membrane, but no finding directly verifying the relationship therebetween has been obtained.

There have been many unclear matters with regard to by what mechanisms the limitation of biotin or the addition of a surfactant or penicillin improves the ability of Coryneform bacteria to produce L-glutamic acid.

In addition, no information on the gene level, which will be an important key factor for clarifying these mechanisms, has been available.

DISCLOSURE OF THE INVENTION

The object of the present invention is to clarify the mechanism of L-glutamic acid-production possessed by Coryneform bacteria, specifically the function of the surfactant to be added in the mechanism of L-glutamic acid production possessed by Coryneform bacteria, and to breed and improve Coryneform bacteria producing L-glutamic acid and the like on the basis of the information thus obtained.

Specifically, the object of the present invention is to clarify, on the gene level, the mechanisms of L-glutamic acid-production by Coryneform bacteria, to isolate a gene of Coryneform bacteria that participates in surfactant resistance, and to apply the thus-obtained gene to the breeding of L-glutamic acid-producing Coryneform bacteria and to the production of L-glutamic acid and the like by Coryneform bacteria.

The present inventors have intensively studied so as to attain the above-mentioned object and, as a result, have found the existence of a gene which will participate in the L-glutamic acid-production by Coryneform bacteria (the gene is hereinafter referred to as dtsR gene, and the protein encoded by the gene is referred to as DTSR protein). In addition, we have found a valuable use for this gene. On the basis of these findings, we have completed the present invention.

The present invention includes the following embodiments:

(1) A gene derived from a Coryneform bacterium and coding for a protein which imparts surfactant resistance to said bacterium.

(2) The gene according to (1), wherein the protein comprises an amino acid sequence of amino acid number 37 to 543 in the amino acid sequence shown by SEQ ID NO: 2 in the Sequence Listing, or an amino acid sequence having, in the amino acid sequence, substitution, deletion or insertion which does not substantially adversely affect on activity to impart the surfactant resistance to Coryneform bacteria.

(3) The gene according to (1), which has a sequence of from 467th to 1987th nucleotides in the nucleotide sequence shown by SEQ ID NO: 1 in the Sequence Listing, or a nucleotide sequence which is substantially the same as the sequence.

(4) A recombinant DNA obtainable by ligating a vector which functions in Coryneform bacteria to the gene as defined in (1), (2) or (3).

(5) A Coryneform bacterium harboring the recombinant DNA as defined in (4).

(6) A method for producing L-lysine comprising cultivating a Coryneform bacterium harboring the recombinant DNA as defined in (4) and capable of producing L-lysine in a liquid medium to produce and accumulate L-lysine in the culture, and collecting the L-lysine.

(7) A gene comprising a nucleotide sequence having substitution, deletion, insertion, addition or inversion of one or more nucleotides in a nucleotide sequence of the gene as defined in (1), (2) or (3) so that a protein encoded by the nucleotide sequence does not normally function regarding an activity to impart surfactant resistance to Coryneform bacteria.

(8) A recombinant DNA obtainable by ligating a vector which functions in Coryneform bacteria to the gene as defined in (7).

(9) A Coryneform bacterium having substitution, deletion, insertion, addition or inversion of one or more nucleotides in a nucleotide sequence of the gene as defined in (1), (2) or (3) or a promoter thereof on chromosome so that a protein having an activity to impart surfactant resistance to Coryneform bacteria does not normally function.

(10) A method for producing L-glutamic acid comprising cultivating a Coryneform bacterium having substitution, deletion, insertion, addition or inversion of one or more nucleotides in a nucleotide sequence of the gene as defined in (1), (2) or (3) or a promoter thereof on chromosome so that a protein having an activity to impart surfactant resistance to Coryneform bacteria does not normally function, and capable of producing L-glutamic acid, in a liquid medium to produce and accumulate L-glutamic acid in the culture, and collecting the L-glutamic acid.

The present invention will be described in detail hereinunder.

Coryneform bacteria as referred to herein are a group of microorganisms defined in Bergey's Manual of Determinative Bacteriology, 8th Ed., p. 599 (1974). The bacteria are aerobic, Gram-positive, non-acid-fast bacilli not having the ability to sporulate, and include bacteria which had been classified as bacteria belonging to the genus Brevibacterium but have now been unified into the genus Corynebacterium [see Int. J. Syst. Bacteriol., 41, 255 (1981)] and also include bacteria of the genus Brevibacterium and Microbacterium which are closely related to the genus Corynebacterium. Of such Coryneform bacteria, those mentioned below, which are known as L-glutamic acid-producing bacteria, are most preferred for use in the present invention.

*Corynebacterium acetoacidophilum*
*Corynebacterium acetoglutamicum*
*Corynebacterium callunae*
*Corynebacterium glutamicum*
*Corynebacterium lilium* (*Corynebacterium glutamicum*)
*Corynebacterium melassecola*
*Brevibacterium divaricatum* (*Corynebacterium glutamicum*)
*Brevibacterium lactofermentum* (*Corynebacterium glutamicum*)
*Brevibacterium saccharolyticum*
*Brevibacterium immariophilium*
*Brevibacterium roseum*
*Brevibacterium flavum* (*Corynebacterium glutamicum*)
*Brevibacterium thiogenitalis*

Specifically, the following strains of these bacteria are exemplified:

| | |
|---|---|
| *Corynebacterium acetoacidophilum* | ATCC 13870 |
| *Corynebacterium acetoglutamicum* | ATCC 15806 |
| *Corynebacterium callunae* | ATCC 15991 |
| *Corynebacterium glutamicum* | ATCC 13032 |
| *Corynebacterium glutamicum* | ATCC 13060 |
| *Brevibacterium divaricatum* | ATCC 14020 |
| *Brevibacterium lactofermentum* | ATCC 13869 |
| *Corynebacterium lilium* | ATCC 15990 |
| *Corynebacterium melassecola* | ATCC 17965 |
| *Brevibacterium saccharolyticum* | ATCC 14066 |
| *Brevibacterium immariophilium* | ATCC 14068 |
| *Brevibacterium roseum* | ATCC 13825 |
| *Brevibacterium flavum* | ATCC 13826 |
| *Brevibacterium thiogenitalis* | ATCC 19240 |

These strains can be obtained from the American Type Culture Collection (ATCC) 10,801 University Blvd., Manassas, Va. 20110-2209. A registration number has been assigned to each strain of bacteria. Based on the registration number, anyone can obtain the corresponding strain of bacteria from ATCC. The registration numbers of the strains of bacteria deposited in ATCC are described in the ATCC catalog.

Surfactants as referred in the present invention function to accelerate the production of L-glutamic acid by Coryneform bacteria, like penicillin, in a medium containing an excess amount of biotin therein, and these include various nonionic surfactants, cationic surfactants and anionic surfactants [see K. Yamada, J. Takahashi and J. Nakamura, the Hakkokogaku Kaishi, 20, 348–350 (1962); K. Udagawa, S. Abe and I. Kinoshita, Hakkokogaku Kaishi, 40, 614–619 (1962)]. Of nonionic surfactants, Tween 60 (polyoxyethylene sorbitan monostearate) and Tween 40 (polyoxyethylene sorbitan monopalmitate) have a penicillin-like effect [see I. Shiio, S. Otsuka and N. Katsuya, J. Biochem., 53, 333–340 (1963)]. $C_3$ to $C_{18}$ free saturated fatty acids have the same effect by themselves [see K. Takinami, H. Okada and T. Tsunoda, Agr. Biol. Chem., 28, 114–118 (1964)]. Tween 40 was used in the examples of the present invention.

<1> Isolation of a gene from a Coryneform bacterium participating in surfactant resistance To isolate a gene from a Coryneform bacterium participating in surfactant resistance, for example, the following process can be employed.

(1) A surfactant-sensitive mutant of a Coryneform bacterium which shows higher sensitivity with regard to surfactants is obtained;

(2) various fragments of a chromosomal DNA prepared from a wild type strain of a Coryneform bacterium are each ligated to a vector that functions in Coryneform bacteria to produce various recombinant DNAs;

(3) the recombinant DNAs each are introduced into cells of the surfactant-sensitive mutant of a Coryneform bacterium to conduct transformation;

(4) from the resulting transformants, strains which have lost the surfactant-sensitivity are selected;

(5) the recombinant DNAs are recovered from the thus-selected surfactant-insensitive transformants; and (6) the structure of the chromosomal DNA fragment of the wild type strain of a Coryneform bacterium ligated to the vector is analyzed.

The chromosomal DNA fragment of the wild type strain of a Coryneform bacterium thus obtained contains a gene derived from a Coryneform bacterium participating in surfactant resistance. This gene participates at least in the mechanism of the accumulation of L-glutamic acid by Coryneform bacteria in a medium containing a surfactant. In addition, this gene also participates in the production of L-glutamic acid in a medium containing penicillin or containing a limited amount of biotin.

A surfactant-sensitive mutant of a Coryneform bacterium which shows higher sensitivity to surfactants means a mutant of a Coryneform bacterium which grows poorly in a medium containing a surfactant at such a concentration that does not have any influence on the growth of the wild type strain of Coryneform bacteria in the medium. Regarding a surfactant of polyoxyethylene sorbitan monopalmitate, a surfactant-sensitive mutant of a Coryneform bacterium grows worse than the corresponding wild type strain in a medium containing the surfactant at a concentration of from 0.1 to 1 mg/dl. On the contrary, the growth of a wild type strain of a Coryneform bacterium is not affected by the presence of the surfactant at a concentration of from 0.1 to 1 mg/dl in the medium. When such a mutant is cultivated in a medium containing an excess amount of biotin to produce L-glutamic acid therein by adding a surfactant, the necessary concentration of the surfactant to be added to the medium may be lower than that in the ordinary case. It is considered that the condition of the cells of the surfactant-sensitive mutant will be similar to that of the cells of the corresponding wild type strain which are exposed to the surfactants.

To obtain a surfactant-sensitive mutant of a Coryneform bacterium, the method described in Japanese Patent Application Laid-Open No. 50-126877 (1975) (Japanese Patent Publication No. 52-24593 (1977)) can be employed.

As one example of the surfactant-sensitive mutant of a Coryneform bacterium, mentioned is Brevibacterium lactofermentum (Corynebacterium glutamicum) AJ 11060. This mutant was deposited in the National Institute of Bioscience and Human-Technology, Agency of Industrial Science and Technology, Ministry of International Trade and Industry, under the accession number FERM P-3678.

To prepare various fragments of the chromosomal DNA of a wild type strain of a Coryneform bacterium, the following process may be employed. The wild type strain of a Coryneform bacterium is cultivated in a liquid medium, the cells grown therein are collected, and the chromosomal DNA is recovered from the collected cells according to the method of Saito et al. [see H. Saito and K. Miura, Biochem. Biophys., Acta 72, 619 (1963)]. The thus-recovered chromosomal DNA is partially cleaved with restriction enzymes. Four-base recognition enzymes are used as the restriction enzymes, and the cleavage is conducted to prepare various DNA fragments under the condition under which the DNA is incompletely decomposed.

The vector functioning in Coryneform bacteria as referred to herein is, for example, a plasmid which is autonomously replicable in Coryneform bacteria. Specific examples of the vector are mentioned below.

| | |
|---|---|
| pAM 330 | see Japanese Patent Application Laid-Open No. 58-67699 (1983) |
| pHM 1519 | see Japanese Patent Application Laid-Open No. 58-77895 (1983) |
| pAJ 655 | see Japanese Patent Application Laid-Open No. 58-192900 (1983) |
| pAJ 611 | see Japanese Patent Application Laid-Open No. 58-192900 (1983) |
| pAJ 1844 | see Japanese Patent Application Laid-Open No. 58-192900 (1983) |
| pCG 1 | see Japanese Patent Application Laid-Open No. 57-134500 (1982) |
| pCG 2 | see Japanese Patent Application Laid-Open No. 58-35197 (1983) |
| pCG 4 | see Japanese Patent Application Laid-Open No. 57-183799 (1982) |
| pCG 11 | see Japanese Patent Application Laid-Open No. 57-183799 (1982) |

To prepare various recombinant DNAs by ligating the vector functioning in Coryneform bacteria and various fragments of the chromosomal DNA of a wild type strain of Coryneform bacteria, the following process may be employed. The vector is first cleaved with a restriction enzyme. The restriction enzyme to be used for cleaving the vector is the same as that used for cleaving the chromosomal DNA, or is such one by which the vector is cleaved to give ends complementary to the ends of the fragment of the chromosomal DNA. The ligation of the vector and the DNA fragment is generally effected via a ligase, such as T4 DNA ligase, etc.

To introduce the recombinant DNA to the surfactant-sensitive mutant of a Coryneform bacterium, any known transformation methods can be employed. For instance, employable are a method of treating recipient cells with calcium chloride so as to increase the permeability of DNA, which has been reported for Escherichia coli K-12 [see Mandel, M. and Higa, A., J. Mol. Biol., 53, 159 (1970)]; and a method of preparing competent cells from cells which are at the growth phase followed by introducing the DNA thereinto, which has been reported for Bacillus subtilis [see Duncan, C. H., Wilson, G. A. and Young, F. E., Gene, 1, 153 (1977)]. In addition to these, also employable is a method of making DNA-recipient cells into the protoplast or spheroplast which can easily take up recombinant DNAs followed by introducing the recombinant DNA into the cells, which is known to be applicable to Bacillus subtilis, actinomycetes and yeasts [see Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)].

The above-mentioned protoplast method for Bacillus subtilis can be employed in the present invention to obtain sufficiently high-level frequency. In addition to this, however, also employable is a method of introducing a DNA into protoplast of cells of a Coryneform bacterium while the protoplast are kept in contact with either polyethylene glycol or polyvinyl alcohol and with divalent metal ions, as described in Japanese Patent Application Laid-Open No. 57-183799 (1982). In this method, carboxymethyl cellulose, dextran, Ficoll, Pluronic F68 (produced by Serva Co.), etc. may also be used, in place of polyethylene glycol or polyvinyl alcohol, so as to accelerate the introduction of DNA to the protoplast cells. In the examples of the present invention, the transformation was conducted by an electric pulse method (see Japanese Patent Application Laid-Open No. 2-207791 (1990)).

The method for selecting the strain which has lost the surfactant sensitivity from the transformants will be described below.

DNA fragments having a size of approximately from 4 to 6 kbp, which have been obtained by partially digesting the chromosomal DNA of a wild type strain of a Coryneform bacterium with the restriction enzyme, Sau3AI, are ligated to a plasmid vector which is autonomously replicable both in Escherichia coli and in Coryneform bacteria to construct recombinant DNAs, and these recombinant DNAs are introduced into the competent cells of Escherichia coli DH5 (produced by Takara Shuzo Co., Ltd.). The resulting transformants are cultivated to prepare a gene library of the wild type strain of a Coryneform bacterium.

By using the recombinant DNA in this gene library, Brevibacterium lactofermentum AJ 11060 is transformed. The resulting transformants are inoculated on a surfactant-free M-CM2G agar plate (containing 5 g of glucose, 10 g of polypeptone, 10 g of yeast extract, 5 g of NaCl, 0.2 g of DL-methionine, 15 g of agar and 4 mg of chloramphenicol in one liter of water, and having a pH of 7.2), and about 40,000 colonies are formed thereon. These colonies are replicated onto a M-CM2G plate containing 30 mg/liter of a surfactant, Tween 40, and the colonies growing well on this surfactant-containing M-CM2G plate are collected. Thus, transformants which have lost the surfactant sensitivity are obtained.

To recover the recombinant DNAs from the thus-obtained transformants which have lost the surfactant sensitivity, the same method as that employed for preparing the chromosomal DNA of the wild type strain of a Coryneform bacterium may be employed. Briefly, the transformants are cultivated in a liquid medium, the cells are collected from the culture, and the recombinant DNAs are recovered from them according to the method of Saito et al. [see H. Saito and K. Miura, Biochem. Biophys., Acta 72, 619 (1963)].

The structure of the chromosomal DNA fragment of the wild type strain of a Coryneform bacterium that has been ligated to the vector is analyzed as follows. The full-length nucleotide sequence of the chromosomal DNA fragment is determined by the dideoxy method which is an ordinary nucleotide sequencing method, and the structure of the DNA is analyzed to determine the positions of the enhancer, the promoter, the operator, the SD sequence, the leader peptide, the attenuator, the initiation codon, the termination codon, the open reading frame, etc.

The gene obtained from the Coryneform bacterium participating in surfactant resistance is dtsR gene, which has a sequence ranging between the 467th to 469th nucleotides (ATG) and 1985th to 1987th nucleotides (CTG) shown by SEQ ID NO: 1 in the Sequence Listing. The amino acid sequence which may be encoded by the gene is shown in SEQ NO: 1 and SEQ NO: 2 in the Sequence Listing. Another ATG (nucleotide number 359–361) is present at the upstream of the ATG of 467th to 469th nucleotides in the same frame and possibility of this ATG being an initiation codon is not denied. However, from analysis of consensus sequence in the upstream region of the gene, it is presumed that the ATG of 467th to 469th nucleotides is an initiation codon. That is, the amino acid sequence of amino acid number 37 to 543 in the amino acid sequence shown by SEQ ID NO: 2 is presumed to be the amino acid sequence of the DTSR protein. When the amino acid sequence of the DTSR protein and the nucleotide sequence of dtsR gene are referred to in the present specification and claims, these may be described with ATG of 467th to 469th nucleotides as the initiation codon. However, it should be considered possibility of the ATG of 359th to 361st nucleotides being the initiation codon. For example, if the dtsR gene is introduced to a Coryneform bacterium to enhance the expression, expression of the sequence of nucleotide number 467 to 1987 in the nucleotide sequence shown by SEQ ID NO: 1 is considered to be sufficient. However, one skilled in the art will easily appreciate that when the coding region and the upstream region of the nucleotide sequence shown by SEQ ID NO: 1 including nucleotide number 359–466 are introduced to a Coryneform bacterium, the DTSR protein can be properly expressed whichever ATG is the initiation codon. In either case, the N-terminal methionine coded by the initiation codon can be cleaved with an aminopeptidase in the expression of the dtsR gene in the cells.

According to the search on data base, it has been confirmed that the dtsR gene having the nucleotide sequence shown by SEQ ID NO: 1 and the DTSR protein encoded by this sequence are novel. It has been found that this protein is homologous to the protein described in Proc. Natl. Acad. Sci. USA, 83, 8049–8053 (1986); Proc. Natl. Acad. Sci. USA, 83, 4864–4869 (1986); and Gene, 122, 199–202 (1992), as propionyl-CoA carboxylase (PCC) β subunit protein. However, none of these references suggests that the protein participates in the production of glutamic acid.

Propionyl-CoA carboxylase is an enzyme that catalyzes one reaction in the metabolic pathway in which α-ketoglutaric acid is converted into succinyl-CoA via 2-hydroxyglutaric acid, propionyl-CoA, D-methylmalonyl-CoA and L-methylmalonyl-CoA, and it seems that the metabolic pathway is a by-pass route for the reaction to be catalyzed by α-ketoglutarate dehydrogenase in the TCA cycle. In this connection, it should be specifically noted that propionyl-CoA carboxylase is an enzyme needing biotin as a coenzyme, indicating that the production of glutamic acid in the surfactant-addition method is related to the production of glutamic acid in the biotin-limitation method.

<2> Preparation of a Coryneform bacterium having the recombinant DNA

The recombinant DNA containing the dtsR gene from a Coryneform bacterium participating in surfactant resistance, which is obtained in the foregoing item <1>, is prepared in vitro, and is introduced into Coryneform bacteria. By the introduction, a Coryneform bacterium can be prepared in which the intracellular concentration of the DTSR protein is increased. The general means for this purpose is to enhance the intracellular expression of the dtsR gene or to increase the number of copies of the dtsR gene in the cells.

To enhance the intracellular expression of the dtsR gene, the gene is ligated downstream of a strong promoter. The dtsR gene is exemplified by a nucleotide sequence which codes for an amino acid sequence of amino acid number 37 to 543 in the amino acid sequence shown by SEQ ID NO: 2. Specifically, a nucleotide sequence of nucleotide number 467 to 1987 in the nucleotide sequence shown by SEQ ID NO: 1 and a nucleotide sequence which is substantially the same as the nucleotide sequence are mentioned. The term "nucleotide sequence which is substantially the same" used herein means a nucleotide sequence coding for a protein which is substantially the same as the protein encoded by the nucleotide sequence of nucleotide number 467 to 1987 with respect to the activity to impart surfactant resistance to Coryneform bacteria. As to these nucleotide sequences, the coded DTSR protein may have substitution, deletion or insertion of an amino acid which does not substantially affect on the activity to impart surfactant resistance to Coryneform bacteria.

As strong promoters functioning intracellularly in Coryneform bacteria, known are the lac promoter, tac promoter and Trp promoter derived from *Escherichia coli* [see Y. Morinaga, M. Tsuchiya, K. Miwa and K. Sano, J. Biotech., 5, 305–312 (1987)]. The trp promoter derived from a Coryneform bacterium is also preferred (see Japanese Patent Application Laid-Open No. 62-195294 (1987)).

The DNA containing the dtsR gene and the DNA containing such a promoter are prepared separately, and these are ligated to each other in vitro. To cleave these DNAs and to ligate them together, restriction enzymes and a ligase are employed, respectively. The recombinant DNA obtained by the ligation is then introduced into cells of a Coryneform bacterium. For the introduction, the same process as that referred to in the foregoing item <1> can be employed.

To introduce the recombinant DNA comprising a strong promoter and the dtsR gene into cells of a Coryneform bacterium, a vector functioning in the cells of the Coryneform bacterium must be used. When the vector referred to in item <1> is used in this step, the recombinant DNA is held outside the chromosome. In order to make the recombinant DNA hold onto the chromosomal DNA, a temperature-sensitive plasmid such as that described in Japanese Patent Application Laid-Open No. 5-7491 (1993) is used as the vector, and the cells are cultivated at a nonpermissible temperature to cause homologous recombination.

The expression of the dtsR gene by the thus-obtained cells of the Coryneform bacterium having therein the recombinant DNA comprising a strong promoter and the dtsR gene is enhanced and the intracellular concentration of the DTSR protein is increased.

When the DNA containing the dtsR gene is ligated to a multi-copy plasmid and introduced into cells of a Coryneform bacterium, the number of copies of the said gene in the cells is increased. As examples of such a multi-copy plasmid, those mentioned in item <1> are referred to.

Also, employable is a process for causing homologous recombination by using, as a target, a sequence that exists in large numbers on the chromosomal DNA of a Coryneform bacterium. As one example of the sequence much existing on the chromosomal DNA of the Coryneform bacterium, mentioned is an insertion sequence existing at both ends of the transposal element of the Coryneform bacterium. The sequence and a method of causing such homologous recombination by using the sequence are disclosed in International Publication No. WO 93/18151.

The expression of the dtsR gene by the thus-obtained cells of a Coryneform bacterium in which the number of copies of the dtsR gene has been increased is enhanced, and the intracellular concentration of the DTSR protein is increased.

<3> Production of L-lysine by Coryneform bacteria having the recombinant DNA therein Various artificial mutants have heretofore been used as L-lysine-producing bacteria. Using these as the hosts, the recombinant DNA of the present invention can be introduced into them to improve their L-lysine productivity. Such artificial mutants are as follows:

S-(2-aminoethyl)-cysteine (hereinafter referred to as "AEC")-resistant mutants; mutants requiring amino acids such as L-homoserine for their growth (see Japanese Patent Publication Nos. 48-28078 (1973) and 56-6499 (1981)); mutants resistant to AEC and requiring amino acids such as L-leucine, L-homoserine, L-proline, L-serine, L-arginine, L-alanine, L-valine, etc. (see U.S. Pat. Nos. 3,708,395 and 3,825,472);

L-lysine-producing mutants resistant to DL-α-amino-ε-caprolactam, α-amino-lauryl-lactam, aspartic acid analogues, sulfa drugs, quinoids and N-lauroyl-leucine, and L-lysine-producing mutants resistant to oxaloacetate decarboxylase inhibitors or respiratory system enzyme inhibitors (see Japanese Patent Application Laid-Open Nos. 50-53588 (1975), 50-31093 (1975), 52-102498 (1977), 53-9394 (1978), 53-86089 (1978), 55-9783 (1980), 55-9759 (1980), 56-32995 (1981), 56-39778 (1981), Japanese Patent Publication Nos. 53-43591 (1978) and 53-1833 (1978));

L-lysine-producing mutants requiring inositol or acetic acid (see Japanese Patent Application Laid-Open Nos. 55-9784 (1980) and 56-8692 (1981)); L-lysine-producing mutants sensitive to fluoropyruvic acid or to temperatures of 34° C. or higher (see Japanese Patent Application Laid-Open No. 53-86090 (1978));

L-lysine-producing mutants of Brevibacterium or Corynebacterium resistant to ethylene glycol (see U.S. Pat. No. 4,411,997).

As specific examples, the following strains are referred to.

Brevibacterium lactofermentum AJ 12031 (FERM BP-277); see Japanese Patent Application Laid-Open No. 60-62994 (1985).

Brevibacterium lactofermentum ATCC 39134; see Japanese Patent Application Laid-Open No. 60-62994 (1985).

Corynebacterium glutamicum AJ 3463 (FERM P-1987); see Japanese Patent Publication No. 51-34477 (1976).

Brevibacterium lactofermentum AJ 12435 (FERM BP-2294); see U.S. Pat. No. 5,304,476.

Brevibacterium lactofermentum AJ 12592 (FERM BP3239); see U.S. Pat. No. 5,304,476.

Corynebacterium glutamicum AJ 12596 (FERM BP-3242); see U.S. Pat. No. 5,304,476.

In the Coryneform bacterium obtained by introducing the recombinant DNA of the present invention into these L-lysine-producing bacteria according to the process in the foregoing item <2>, the intracellular concentration of the DTSR protein is increased, and the resultant bacterium has the ability to produce a large amount of L-lysine.

The medium used for the production of L-lysine may be ordinary medium containing carbon sources, nitrogen sources, inorganic ions and, if desired, other minor organic nutrients.

Saccharides such as hydrolysates of starch, etc.; alcohols such as ethanol, inositol, etc.; organic acids such as acetic acid, fumaric acid, citric acid, succinic acid, etc are usable.

As the nitrogen sources, usable are inorganic ammonium salts such as ammonium sulfate, ammonium chloride, ammonium phosphate, etc.; organic nitrogen compounds such as hydrolysates of soybeans, etc.; as well as ammonia gas, aqueous ammonia, etc.

As the inorganic ions, small amounts of potassium phosphate, magnesium sulfate, iron ions, manganese ions, etc. are added to the medium. As the minor organic nutrients, essential substances such as vitamin Bi, etc., as well as yeast extract, etc are preferably contained in suitable amounts, if necessary.

It is recommended that the cultivation is performed under an aerobic condition for 16 to 72 hours at a temperature ranging from 30 to 45° C., and during the cultivation, the pH of the media is controlled to between 5 and 7. To adjust the pH, inorganic or organic, acidic or alkaline substances, ammonia gas, etc. can be used.

The collection of L-lysine from the fermentation liquid may be conducted by an ordinary ion-exchange method, a precipitation method and other known methods in combination.

<4> Preparation of Coryneform bacteria in which the DTSR protein does not normally function The dtsR gene has been obtained as a gene that imparts resistance to surfactants to a Coryneform bacteria, as mentioned in the foregoing item <1>. Therefore, it was expected that the strain with the amplified dtsR gene would no longer produce L-glutamic acid in a medium to which a surfactant was added at a concentration at which the wild type strain of a Coryneform bacterium produces L-glutamic acid in the presence of an excess amount of biotin. In consideration of this, the effect of the amplification of the dtsR gene in the production of L-glutamic acid by adding a surfactant was investigated according to the method shown in the examples described below, and, as was expected, the noticeable inhibition of the production of L-glutamic acid was observed. In addition, it was confirmed that the amplification of the dtsR gene also resulted in the suppression of the production of L-glutamic acid in the biotin-limiting method and in the penicillin-adding method in the presence of an excess amount of biotin. These results indicate that the dtsR gene does not only make the strain resistant to surfactants but also plays an important role in the production of L-glutamic acid.

For these reasons, it was expected that if, opposite to the above, the expression of the dtsR gene is inhibited and the intracellular concentration or activity of the DTSR protein is lowered, the ability of the cells to produce L-glutamic acid might be improved and L-glutamic acid might be produced especially in a medium containing an excess amount of biotin without adding any biotin activity-suppressing substance such as surfactants or antibiotics. In consideration of this, a strain in which the dtsR gene of the wild type strain was disrupted was prepared and the ability of the thus-modified strain to produce L-glutamic acid was examined, and it has been confirmed that the dtsR gene-disrupted mutant strain produced a large amount of L-glutamic acid even if biotin is present at a high concentration at which the wild type strain produces little L-glutamic acid, as is demonstrated in the examples as described below.

The strain in which the dtsR gene is mutated can be obtained by a method inducing mutation by use of a chemical agent or by a breeding method using recombinant DNA technique. When the gene has already been obtained, the recombinant DNA technique is employed, whereby the gene can easily be disrupted by homologous recombination. The means of disrupting a gene by homologous recombination has already been established. For this, employable are a method of using a linear DNA and a method of using a temperature-sensitive plasmid.

Specifically, by site-specific mutation [see Kramer, W. and Faits, H. J., Methods in Enzymology, 154, 350 (1987)] or mutation with chemicals such as sodium hyposulfite, hydroxylamine, etc. [see Shortle, D. and Nathans, D., Proc. Natl. Acad. Sci. USA, 75, 270 (1978)], the substitution, deletion, insertion, addition or inversion of one or more nucleotides is made in the nucleotide sequence of the coding region or of the promoter region in the dtsR gene. The thus-modified or disrupted gene is substituted for the normal gene on the chromosome, thereby lowering or vanishing the activity of the genetic product, DTSR protein, or lowering or vanishing the transcription of the gene.

In the site-specific mutagenesis, synthetic oligonucleotides are used, and according to this method, it is possible to introduce any desired substitution, deletion, insertion, addition or inversion to only (a) limited base pair(s). To carry out this method, a plasmid having the intended gene which has been cloned and whose nucleotide sequence has been determined, is first denatured to prepare a single-stranded DNA. Next, a synthetic oligonucleotide complementary to the site to be mutated is prepared. The synthetic oligonucleotide shall be such that it does not have a completely complementary sequence but may have any desired nucleotide substitution, deletion, insertion, addition or inversion. After this, the single-stranded DNA is annealed with the synthetic oligonucleotide having such a desired nucleotide substitution, deletion, insertion, addition or inversion. Then, this is formed into a complete double-stranded plasmid, using the Klenow fragment of DNA polymerase I and T4 ligase. The resulting plasmid is then introduced into the competent cell of *Escherichia coli*. Some of these transformants thus obtained have a plasmid containing the gene that has the desired nucleotide substitution, deletion, insertion, addition or inversion fixed therein. As a similar method for modifying or disrupting the gene by introducing the mutation, known is the recombinant PCR method [see PCR Technology, Stockton Press (1989)].

The chemical treatment method is a method for directly treating the DNA fragment containing the intended gene with sodium hyposulfite, hydroxylamine or the like chemical thereby randomly introducing the mutation having nucleotide substitution, deletion, insertion, addition or inversion into the DNA fragment.

Whether or not the desired mutation is introduced can be confirmed by transforming a surfactant-sensitive mutant with the DNA fragment subjected to mutation treatment and determining the presence of surfactant resistance of the resultant transformant. On this occasion, by examining growth both at high temperature and at low temperature within temperature at which the Coryneform bacteria can usually grow, and selecting a transformant which can grow at the low temperature and the growth of which is inhibited at higher temperature, a mutated gene which becomes temperature-sensitive can be obtained.

As the means of substituting the thus-obtained gene that has been modified or disrupted by the introduction of the mutation for the normal gene on the chromosome of a Coryneform bacterium, employable is a method of using homologous recombination [see Experiments in Molecular Genetics, Cold Spring Harbor Laboratory Press (1972); Matsuyama, S. and Mizushima, S., J. Bacteriol., 162, 1196 (1985)]. According to homologous recombination, when a plasmid or the like having a sequence which is homologous to the sequence of the chromosome is introduced into the cell, a recombination occurs at the sites having the homologous sequence at a certain frequency whereby the complete plasmid introduced is incorporated into the chromosome. After this, when a further recombination occurs at the sites having the homologous sequence on the chromosome, the plasmid is removed from the chromosome. By the latter recombination, the gene into which the mutation has been introduced is fixed onto the chromosome, depending on the recombined site, and the original normal gene may be removed from the chromosome along with the plasmid. By selecting such a strain, it is possible to obtain a strain in which the gene modified or disrupted by the introduction thereinto of the mutation having nucleotide substitution, deletion, insertion, addition or inversion has been substituted for the normal gene on the chromosome.

<5> Production of L-glutamic acid by Coryneform bacteria in which the DTSR protein does not normally function As described above, a strain which is the L-glutamic acid-producing Coryneform bacterium and in which intracellular concentration or activity the DTSR protein is lowered, that is, a strain in which the DTSR protein does not normally function is improved in productivity of L-glutamic acid. Especially, the strain can produce L-glutamic acid without addition of biotin activity-suppressing substance such as a surfactant or antibiotic even if biotin is present in an excess amount.

For obtaining a mutant in which the DTSR protein does not normally function by breeding Coryneform bacteria having the ability to produce L-glutamic acid, a glutamic acid-producing wild type strain or a mutant derived therefrom of Coryneform bacteria can be used as the starting strain. As examples of the mutant, the following are mentioned:

*Brevibacterium lactofermentum* AJ 12745 (FERM-BP 2922); see U.S. Pat. No. 5,272,067.

*Brevibacterium lactofermentum* AJ 12746 (FERM-BP 2923); see U.S. Pat. No. 5,272,067.

*Brevibacterium flavum* AJ 12747 (FERM-BP 2924); see U.S. Pat. No. 5,272,067.

*Corynebacterium glutamicum* AJ 12478 (FERM-BP 2925); see U.S. Pat. No. 5,272,067.

*Corynebacterium glutamicum* ATCC 21492.

The medium to be used for the production of L-glutamic acid may be ordinary medium containing carbon sources, nitrogen sources, inorganic ions and, if desired, other minor organic nutrients.

As the carbon sources, usable are saccharides such as glucose, lactose, galactose, fructose, hydrolysates of starch, etc.; alcohols such as ethanol, inositol, etc.; organic acids such as acetic acid, fumaric acid, citric acid, succinic acid, etc.

As the nitrogen sources, usable are inorganic ammonium salts such as ammonium sulfate, ammonium chloride, ammonium phosphate, etc.; organic nitrogen compounds such as hydrolysates of soybeans, etc.; as well as ammonia gas, aqueous ammonia, etc.

As the inorganic ions, small amounts of potassium phosphate, magnesium sulfate, iron ions, manganese ions, etc. are added to the medium. As the minor organic nutrients, essential substances such as vitamin $B_1$, etc., as well as yeast extract, etc are preferably contained in suitable amounts, if necessary.

It is recommended that the cultivation is carried out under an aerobic condition for 16 to 72 hours at a temperature ranging from 30 to 45° C., and during the cultivation, the pH of the medium is kept at from 5 to 8. To adjust the pH, inorganic or organic, acidic or alkaline substances, ammonia gas, etc. can be used.

Surfactants or penicillin may be added to the medium where the dtsR gene-disrupted strain thus obtained is cultivated, or the biotin concentration in the medium may be limited. In this way, the yield of L-glutamic acid to be produced in the medium may be increased further.

The collection of L-glutamic acid from the fermentation liquid may be effected by an ordinary ion exchange method, precipitation method and other known methods in combination.

○: pDTR6-introduced strain in surfactant-free medium

□: pSAC4-introduced strain in surfactant-free medium

●: pDTR6-introduced strain in surfactant-added medium

■: pSAC4-introduced strain in surfactant-added medium

Figure 2:
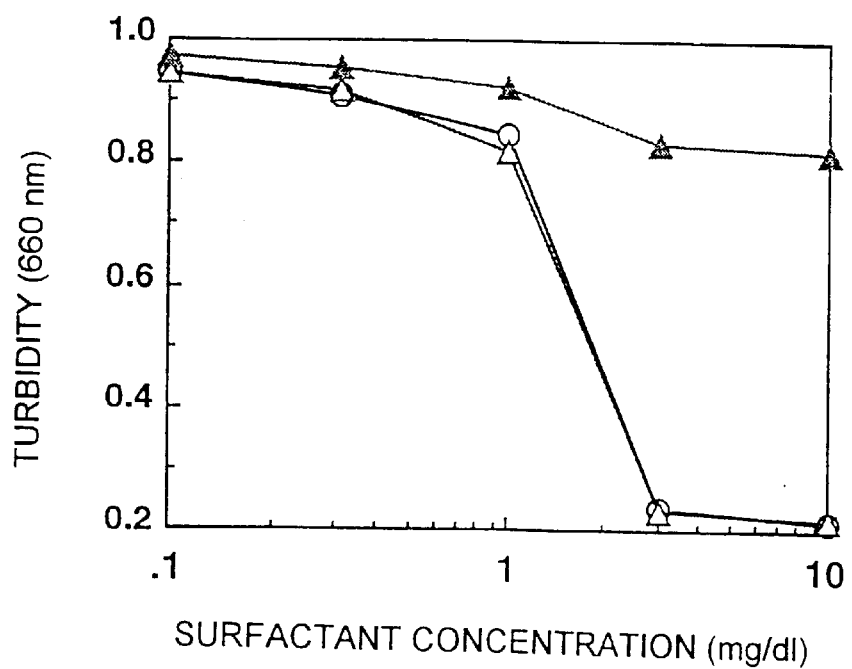

FIG. 2 shows the degree of surfactant resistance of ATCC 13869/pHSGX-KΔE (deletion-mutation type dtsR gene-amplified strain), ATCC 13869/pDTR6 (dtsR gene-amplified strain) and ATCC 13869/pSAC4 (control).

○: pSAC4-introduced strain

Δ: pHSGX-KΔE-introduced strain

▲: pDTR6-introduced strain

Figure 3:
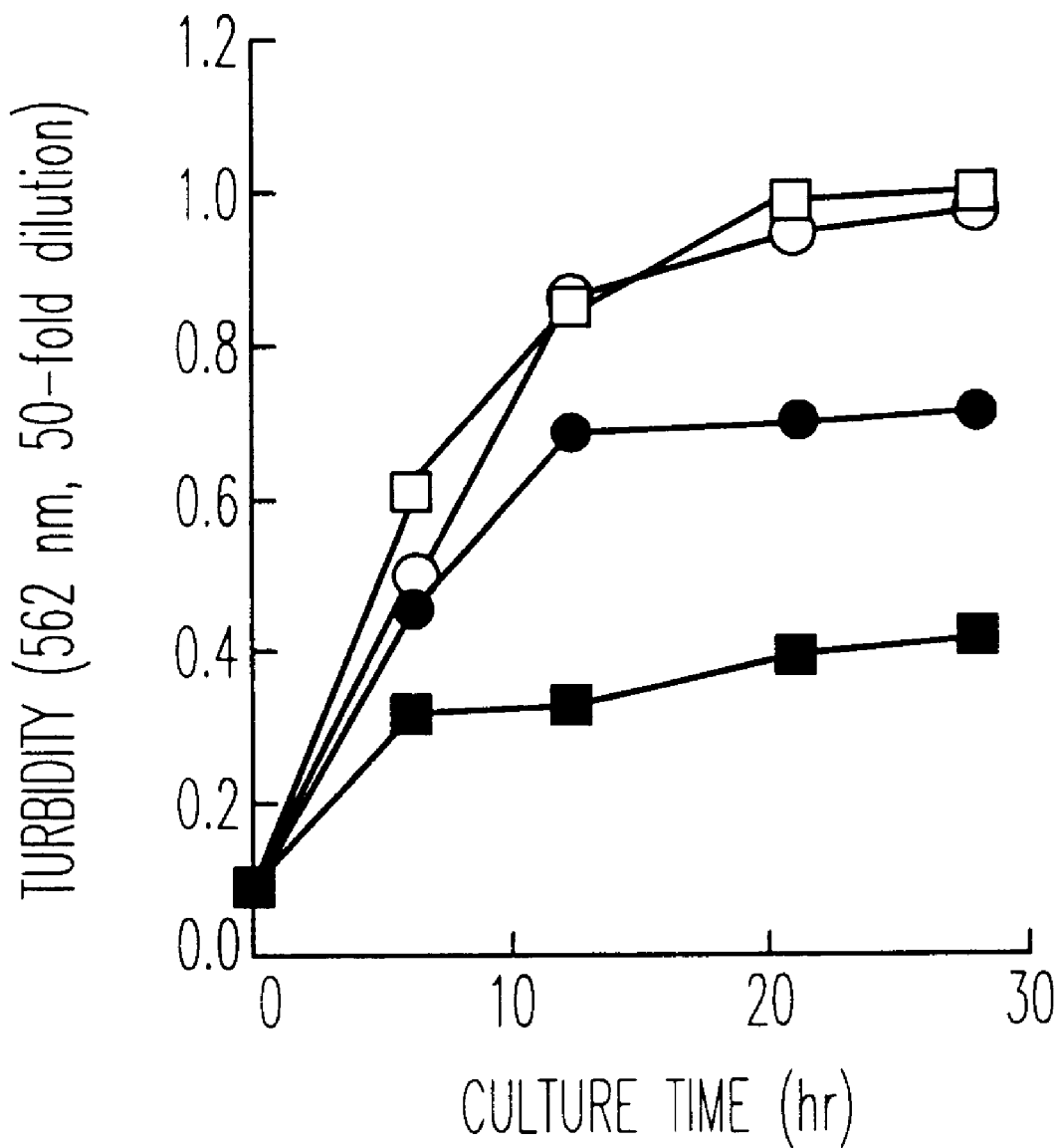

FIG. 3 shows the growth curve of AJ 11060/pDTR6 and AJ 11060/pSAC4 in a medium containing 300 or 3 μg/liter of biotin.

○: pDTR6-introduced strain in the presence of 300 μg/liter of biotin

□: pSAC4-introduced strain in the presence of 300 μg/liter of biotin

●: pDTR6-introduced strain in the presence of 3 μg/liter of biotin

■: pSAC4-introduced strain in the presence of 3 μg/liter of biotin

DESCRIPTION OF THE PREFERRED EMBODIMENT

The present invention will be described in more detail with reference to the following examples.

EXAMPLE 1

(Preparation of chromosomal DNA of *Brevibacterium lactofermentum* ATCC 13869 (a wild type strain of Coryneform bacteria)

*Brevibacterium lactofermentum* ATCC 13869 was inoculated in 100 ml of a T-Y medium [containing 1% Bacto-tripton (by Difco), 0.5% Bacto-yeast extract (by Difco) and 0.5% NaCl; pH 7.2] and cultivated at 31.5° C. for 8 hours to obtain a culture. This culture was subjected to centrifugation at 3,000 r.p.m. for 15 minutes to obtain 0.5 g of wet cells.

From the wet cells, obtained was the chromosomal DNA according to Saito & Miura method (see Biochem. Biophys. Acta. 72, 619, (1963)). Next, 60 μg of the chromosomal DNA and 3 units of a restriction enzyme, Sau3AI were each mixed in 10 mM Tris-HCl buffer (containing 50 mM NaCl, 10 mM $MgSO_4$ and 1 mM dithiothreitol; pH 7.4), and the reaction was carried out at 37° C. for 30 minutes. After the reaction, the reaction mixture was subjected to ordinary phenol extraction and ethanol precipitation to obtain 50 μg of chromosomal DNA fragments of *Brevibacterium lactofermentum* ATCC 13869 digested with Sau3AI.

EXAMPLE 2

(Preparation of gene library of *Brevibacterium lactofermentum* ATCC 13869, using plasmid vector DNA)

20 μg of a plasmid vector DNA (pSAC4) capable of autonomously replicating in both the cells of *Escherichia coli* and the cells of Coryneform bacteria and 200 units of a restriction enzyme, BamHI were mixed in 50 mM Tris-HCl buffer (containing 100 mM NaCl and 10 mM magnesium sulfate; pH 7.4) and reacted at 37° C. for 2 hours to obtain a digested solution, and the solution was then subjected to ordinary phenol extraction and ethanol precipitation. After this, the DNA fragment was dephosphorylated with bacterial alkaline phosphatase according to the method described in Molecular Cloning, 2nd Edition [J. Sambrook, E. F. Fritsch and T. Maniatis, Cold Spring Harbor Laboratory Press, p.1.56 (1989)] so as to prevent the re-binding of the plasmid vector-derived DNA fragment, and then the thus-dephosphorylated DNA fragment was subjected to ordinary phenol extraction and ethanol precipitation.

One μg of this pSAC4 digested with BamHI, 1 μg of the chromosomal DNA fragments of *Brevibacterium lactofermentum* ATCC 13869 digested with Sau3AI, that had been obtained in Example 1, and 2 units of T4 DNA ligase (produced by Takara Shuzo Co., Ltd.) were added to 66 mM Tris-HCl buffer (pH 7.5) containing 66 mM magnesium chloride, 10 mM dithiothreitol and 10 mM ATP and reacted therein at 16° C. for 16 hours to conduct the ligation of the DNA. Next, cells of *Escherichia coli* DH5 were transformed with said DNA mixture by an ordinary method, and the resulting transformant cells were inoculated onto an L-agar medium containing 170 μg/ml of chloramphenicol to obtain about 20,000 colonies constituting a gene library.

EXAMPLE 3

(Transformation of *Brevibacterium lactofermentum* AJ 11060)

From these approximately 20,000 colonies mentioned above, the recombinant DNAs were recovered according to the above-mentioned Saito and Miura method.

The recombinant DNA mixture which was divided into 50 batches, was introduced into cells of the strain AJ 11060, a mutant being sensitive to surfactants, by ordinary transformation using electric pulse (see Japanese Patent Application Laid-Open No. 2-207791 (1990)). The resulting transformant cells were inoculated onto a glucose-added L-agar medium and the cultivation was performed by static incubation at 31.5° C., whereby about 20,000 colonies of transformants were formed on the medium. Next, these transformant colonies were replicated to the same plate medium but containing 30 mg/liter of the surfactant, and several strains that were resistant to the surfactant and grown on the plate medium were obtained therefrom.

EXAMPLE 4

(Measurement of surfactant resistance of strains having multi-copies of dtsR gene)

Figure 1:
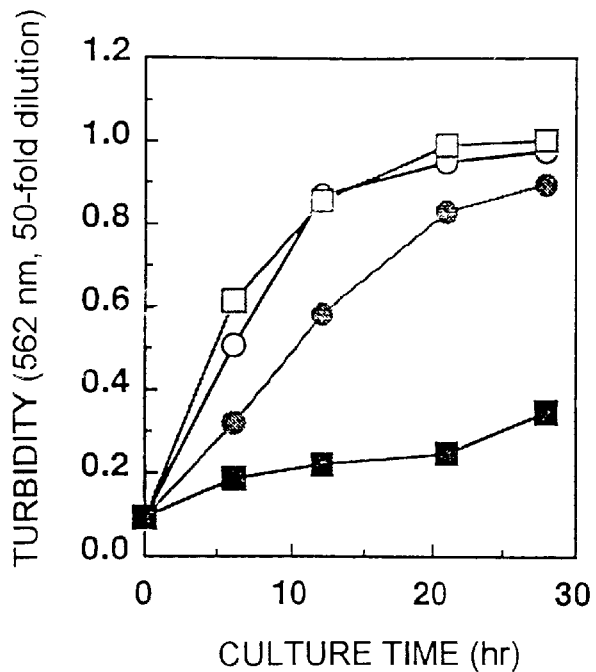
FIG. 1 shows the growth of AJ 11060/pDTR6 (dtsR gene-amplified strain) and AJ 11060/pSAC4 (control) in a surfactant-free or surfactant-added medium.

The recombinant DNA was extracted from each of the several strains that had been grown, and *Brevibacterium lactofermentum* AJ 11060 was re-transformed with the DNA. From the resulting transformants, one surfactant-resistant strain was selected. The recombinant DNA of this strain is designated as pDTR6, and the gene which is carried by this plasmid and which has the ability to make the strain resistant to the surfactant is designated as dtsR. The inhibition of the growth of AJ 11060, into which the plasmid had been introduced, in a surfactant(3 g/liter)-added liquid medium is suppressed (see FIG. 1).

EXAMPLE 5
(Preparation of DNA)

The plasmid was prepared from AJ 11060/pDTR6 having the recombinant DNA that had been obtained in the above, by an ordinary method, and this was introduced into *Escherichia coli* JM 109. The resulting *Escherichia coli* JM 109/pDTR6 was cultivated in 20 ml of a medium containing 1% of tryptone, 0.5% of yeast extract and 0.5% of NaCl, at 37° C. for 24 hours, and 20 ml of the resulting culture was inoculated in one liter of a medium having the same composition as above and cultivation was performed at 37° C. for 3 hours. Then, 0.2 g of chloramphenicol was added thereto, and the cultivation was continued for additional 20 hours at the same temperature to obtain a culture. Next, the resulting culture was centrifuged at 3,000 r.p.m. for 10 minutes to obtain 2 g of wet cells. The obtained cells were suspended in 20 ml of 350 mM Tris-HCl buffer (pH 8.0) containing 25% of sucrose, and then 10 mg of lysozyme (produced by Sigma Co.), 8 ml of 0.25M EDTA solution (pH 8.0) and 8 ml of 20% sodium dodecylsulfate solution were added thereto. Then, the resulting suspension was heated at 60° C. for 30 minutes to obtain a lysate. 13 ml of 5M NaCl solution was added to the lysate, and the lysate was then treated at 4° C. for 16 hours. After the treatment, this was centrifuged at 15,000 r.p.m. for 30 minutes. The supernatant thus obtained was subjected to ordinary phenol extraction and ethanol precipitation to obtain a DNA precipitate.

The precipitate was dried under reduced pressure and then dissolved in 6 ml of 10 mM Tris-HCl buffer (pH 7.5) containing 1 mM EDTA, and 6 g of cesium chloride and 0.2 ml of ethidium bromide (19 mg/ml) were added thereto. Then, this was subjected to equilibrium density gradient centrifugation, using an ultracentrifugater, at 39,000 r.p.m. for 42 hours, by which the DNA was isolated. Next, ethidium bromide was removed from this, using n-butanol, and thereafter this was subjected to dialysis against 10 mM Tris-HCl (pH 7.5) containing 1 mM EDTA to obtain about 500 μg of a purified recombinant DNA, pDTR6. A private number AJ 12967 was assigned to *Escherichia coli* JM109/pDTR6. This strain was deposited on Feb. 22, 1994 in National Institute of Bioscience and Human-Technology, Agency of Industrial Science and Technology, Ministry of International Trade and Industry, with the accession number FERM P-14168, and transferred on Feb. 9, 1995 to the international deposit under the Budapest Treaty with the accession number FERM BP-4994.

EXAMPLE 6
(Analysis of nucleotide sequence of DNA having dtsR gene)

The nucleotide sequence of the recombinant DNA obtained in Example 5 was determined. The sequencing was effected according to the Sanger method, using a Taq DyeDeoxy Terminator Cycle Sequencing Kit (produced by Applied Biochemical Co.). The nucleotide sequence of the DNA thus obtained is shown by SEQ ID NO: 1 in the Sequence Listing. While the longest open reading frame in this sequence is a nucleotide sequence of from 359th A to 1987th G in the nucleotide sequence shown by SEQ ID NO: 1, it is presumed from analysis of consensus sequence in the upstream region of the gene that ATG of 467th to 469th is an initiation codon. The amino acid sequence which can be encoded by the open reading frame of 359th A to 1987th G is shown by SEQ ID NO: 1 in the Sequence Listing together with the nucleotide sequence. Further, only the amino acid sequence is shown by SEQ ID NO: 2 in the Sequence Listing. A protein encoded by the nucleotide sequence of from 467th to 1987th nucleotides is designated as the DTSR protein.

It is well known that the N-terminal methionine residue of protein is deleted after translation by the action of peptidase. This is because the N-terminal methionine is derived from the translation initiation codon, ATG, and therefore has no relation to the intrinsic function of protein in most cases. Also in the DTSR protein of the present invention, there is a probability that the methionine residue is deleted.

The nucleotide sequence and the amino acid sequence were compared with known sequences with respect to the homology. The data bases used for the comparison were EMBL and SWISS-PROT. As a result, it has been confirmed that the gene represented by SEQ ID NO: 1 in the Sequence Listing and the protein encoded by this are novel.

EXAMPLE 7
(Confirmation of participation of dtsR gene in surfactant resistance)

The open reading frame was identified by the nucleotide sequencing, which suggested the existence of DTSR protein. In order to further confirm that the gene which imparts surfactant resistance to Coryneform bacteria exists in this region, a part of gene in the region of the open reading frame was deleted in an in-frame manner from the gene fragment represented by SEQ ID NO: 1 in the Sequence Listing, and this gene fragment was investigated as to whether or not it has an activity of imparting surfactant resistance to Coryneform bacteria. Specifically, pDTR6 was digested with XbaI and KpNI to obtain a fragment containing dtsR gene. This gene fragment was ligated to a fragment of plasmid pHSG398 (produced by Takara Shuzo Co., Ltd.) that had been treated with XbaI and KpnI, using T4 DNA ligase (produced by Takara Shuzo Co., Ltd.), to prepare plasmid pHSGX-K. The dtsR gene has two sites that are digested with Eco52I, at the nucleotides 766 and 1366 in SEQ ID NO: 1. PHSGX-K was completely digested with Eco52I and then self-ligated to prepare plasmid pHSGX-KΔE from which 600 base pairs of the Eco52I fragments were deleted. The structure of the dtsR gene on this pHSGX-KΔE was such that the center part was deleted in an in-frame manner.

Next, in order to make pHSGX-KΔE capable of autonomously replicating in Coryneform bacteria, the replication origin derived from a known plasmid, pHM1519, capable of self-amplification in Coryneform bacteria (see Miwa, K. et al., Agric. Biol. Chem. 48, 2901–2903 (1984); Japanese Patent Application Laid-Open No. 5-7491 1993)) was introduced into the only one KpnI cleavage site existing on pHSGX-KΔE. Specifically, pHM1519 was digested with restriction enzymes, BamH1 and KpnI to obtain a gene fragment having a replication origin, and the resulting fragment was made to have blunt ends, using a blunting kit produced by Takara Shuzo Co., Ltd, and then introduced into the KpnI site of pHSGX-KΔE, using a KpnI linker (produced by Takara Shuzo Co., Ltd.), to obtain pKCX-KΔE. As a control sample, the replication origin of pHM1519 was inserted into the SalI site of pHSG399, using SalI linker (produced by Takara Shuzo Co., Ltd.) to prepare pSAC4. These pKCX-KΔE and pSAC4 prepared herein were separately introduced into cells of a wild type strain of Coryneform bacteria, *Brevibacterium lactofermentum*

ATCC 13869, according to the above-mentioned electric pulse method, and the resulting transformants were examined with respect to the degree of surfactant resistance. For the examination, the cells were cultivated in a M-CM2G liquid medium, to which from 0 to 10 mg/dl of polyoxyethylene sorbitan monopalmitate had been added, and the degree of the cell growth in the culture was measured.

As a result, it was verified that the deletion-type dtsR gene had lost the function to impart the surfactant resistances.

EXAMPLE 8

(Production of L-glutamic acid using dtsR gene-amplified strain by biotin-limiting method)

The strain AJ 11060/pDTR6 was cultivated to produce L-glutamic acid, according to the biotin-limiting method, as mentioned below. Specifically, the strain AJ 11060/pDTR6 was separately cultivated on an M-CM2G plate medium containing 4 mg/liter of chloramphenicol. Then, the grown cells were inoculated in a medium containing 80 g of glucose, 1 g of $KH_2PO_4$, 0.4 g of $MgSO_4 \cdot 7H_2O$, 30 g of $(NH_4)_2SO_4$, 0.01 g of $FeSO_4 \cdot 7H_2O$, 0.01 g of $MnSO_4 \cdot 7H_2O$, 15 ml of soybean hydrolysate solution, 200 μg of thiamine hydrochloride, 60 μg of biotin, 4 mg of chloramphenicol and 50 g of $CaCO_3$ in one liter of pure water (the pH of the medium having been adjusted to 7.0 with KOH) and cultivated therein at 31.5° C. for 20 hours. The resulting culture was inoculated in the same medium as above but not containing biotin (this medium is hereinafter referred to as a "biotin-limited medium"), at a concentration of 5% by volume, and the cultivation was carried out at 31.5° C. for about 20 hours.

While cultivating the strain AJ 11060/pDTR6 in the biotin-limited medium, the amount of biotin required by the unit weight of the cells grown in the medium was measured (see FIG. 3). As a control, the strain AJ 11060/pSAC4 was cultivated in the same manner as above.

The amounts of the grown cells of the strain AJ 11060/pDTR6 were larger than that of the control. Thus, the biotin demand per unit weight of the grown cells of the AJ 11060/pDTR6 was lowered than that of the strain AJ 11060/pSAC4.

EXAMPLE 9

(Production of L-lysine by dtsR aene-amplified strain)

pDTR6 was introduced into an L-lysine-producing strain of Coryneform bacteria, Brevibacterium lactofermentum AJ 12435 (FERM BP-2294), by an electric pulse method. The resulting transformant was cultivated in a medium mentioned below to produce L-lysine.

Specifically, the strain was cultivated on an M-CM2G plate medium containing 4 mg/liter of chloramphenicol, and the thus-obtained cells were inoculated in a medium containing 100 g of glucose, 1 g of $KH_2PO_4$, 0.4 g of $MgSO_4$, 30 g of $(NH_4)_2SO_4$, 0.01 g of $FeSO_4 \cdot 7H_2O$, 0.01 g of $MnSO_4 \cdot 7H_2O$, 15 ml of soybean hydrolysate solution, 200 μg of thiamine hydrochloride, 300 μg of biotin, 4 mg of chloramphenicol and 50 g of $CaCO_3$ in one liter of pure water (the pH of the medium having been adjusted to 7.0 with KOH) at 32° C. for 40 hours. As a control, a strain into which pSAC4 is introduced in the same manner instead of pDTR6 was used. The results are shown in Table 1.

TABLE 1

| Strain | L-lysine (g/liter) |
|---|---|
| AJ 12435/pSAC4 | 15 |
| AJ 12435/pDTR6 | 25 |

REFERENCE EXAMPLE 1

(Production of L-glutamic acid using dtsR gene-amplified strain by surfactant-added method)

By adding a surfactant as a biotin activity-suppressing agent, the strain AJ 11060 can produce a large amount of L-glutamic acid even if a high concentration of biotin is present. However, since dtsR gene-amplified strains have elevated surfactant resistance, it was considered that the production of glutamic acid by these strains will be decreased, even though a surfactant is added. The strains AJ 11060/pSAC4 and AJ 11060/pDTR6 were cultivated to produce L-glutamic acid, according to the surfactant-added method mentioned below. Specifically, the strains were each cultivated on an M-CM2G plate medium containing 4 mg/liter of chloramphenicol. Then, the cells were inoculated onto a medium containing 80 g of glucose, 1 g of $KH_2PO_4$, 0.4 g of $MgSO_4 \cdot 7H_2O$, 30 g of $(NH_4)_2SO_4$, 0.01 g of $FeSO_4 \cdot 7H_2O$, 0.01 g of $MnSO_4 \cdot 7H_2O$, 15 ml of soybean hydrolysate solution, 200 μg of thiamine hydrochloride, 300 μg of biotin, 4 mg of chloramphenicol, 3.0 g of polyoxyethylene sorbitan monopalmitate and 50 g of $CaCO_3$ in one liter of pure water (the pH of the medium having been adjusted to 8.0 with KOH) and cultivated therein at 31.5° C. for 20 hours.

After the cultivation, the amount of L-glutamic acid produced and accumulated in each culture was measured. The yields obtained are shown in Table 2. The yield is shown as a yield of L-glutamic acid based on the sugar added in the medium (weight basis).

TABLE 2

| Strain | Yield of L-glutamic Acid (%) |
|---|---|
| AJ 11060/pSAC4 | 29.6 |
| AJ 11060/pDTR6 | 9.0 |

By amplifying the dtsR gene, the yield of L-glutamic acid remarkably reduced. This indicates that the DTSR protein closely involves in the production of L-glutamic acid by the surfactant-added method.

REFERENCE EXAMPLE 2

(Production of L-glutamic acid using dtsR gene-amplified strain by penicillin-added method)

The strains AJ 11060/pSAC4 and AJ 11060/pDTR6 were cultivated to produce L-glutamic acid by the penicillin-added method in the same manner as in Reference Example 1, except that 30 units of penicillin G was added to the medium in place of polyoxyethylene sorbitan monopalmitate. The results are shown in Table 3.

TABLE 3

| Strain | Yield of L-glutamic Acid (%) |
|---|---|
| AJ 11060/pSAC4 | 27.6 |
| AJ 11060/pDTR6 | 12.8 |

By amplifying the dtsR gene, the yield of L-glutamic acid remarkably reduced. This indicates that the DTSR protein also involves in the production of L-glutamic acid by the penicillin-added method, as well as the production of L-glutamic acid by the surfactant-added method.

EXAMPLE 10

(Production of dtsR gene-disrupted strain)

Since it was found that the production of L-glutamic acid was decreased by the amplification of the dtsR gene, it was

19 expected that the disruption of the dtsR gene would result in an increase in the yield of L-glutamic acid. The gene-disrupted strain was obtained by the homologous recombination method disclosed in Japanese Patent Application Laid-Open No. 5-7491 (1993) using a temperature-sensitive plasmid.

Specifically, the replication origin which had been obtained from a plasmid capable of autonomously replicating in Coryneform bacteria and in which the autonomous replication had become temperature-sensitive, was introduced into the KpnI recognition site of pHSGX-KΔE shown in Example 7, to form plasmid pKTCX-KΔE.

This pKTCX-KΔE was introduced into a wild type strain, *Brevibacterium lactofermentum* ATCC 13869 by an electric pulse method, and the dtsR gene on the chromosome was substituted by a deleted-type dtsR gene according to the method described in Japanese Patent Application Laid-Open No. 5-7491 (1993). Specifially, ATCC 13869/pKTCX-KΔE was cultivated by shaking in a M-CM2G liquid medium containing 50 pg/ml of oleic acid at 25° C. for 6 hours, and the culture was inoculated onto an M-CM2G medium containing 5 μg/ml of chloramphenicol and 50 μg/ml of oleic acid. The plasmid-inserted strains formed colonies at 34° C., and these were collected. From the thus-obtained strains, those that had become sensitive to chloramphenicol at 34° C. were selected by a replication method. The chromosomes of these sensitive strains were obtained by an ordinary method, and the structure of the dtsR gene of each of these chromosomes was analyzed by the Southern hybridization method. Thus, the strain in which the dtsR gene had been substituted by a deleted-type dtsR gene was confirmed and designated as a strain ΔE.

EXAMPLE 11

(Estimation of L-Glutamic acid productivity of the strain ΔE)

20

The strains, ATCC 13869, AJ 11060 and ΔE, were cultivated to produce L-glutamic acid in the manner mentioned below. These strains were each refreshed by cultivating on an M-CM2G plate medium. The thus-refreshed strains were inoculated into a medium containing 80 g of glucose, 1 g of $KH_2PO_4$, 0.4 g of $MgSO_4$, 30 g of $(NH_4)_2SO_4$, 0.01 g of $FeSO_4.7H_2O$, 0.01 g of $MnSO_4.7H_2O$, 15 ml of soybean hydrolysate, 200 μg of thiamine hydrochloride, 300 μg of biotin, 1 g of Tween 80 (polyoxyethylene sorbitan monooleate) and 50 g of CaCO3 in one liter of pure water (the pH of the medium having been adjusted to 8.0 with KOH), and the cultivation was carried out at 31.5° C. for 20 hours. The results are shown in Table 4.

TABLE 4

| Strain | L-Glutamic Acid (g/liter) |
|---|---|
| ATCC 13869 | 0 |
| AJ 11060 | 0 |
| ΔE | 34 |

With respect to the wild type strain and the strain AJ 11060, the accumulation of L-glutamic acid was not observed due to biotin present in an excess amount in the medium. In contrast, the strain ΔE well produced and accumulated L-glutamic acid.

Industrial Applicability

The dtsR gene of the present invention is a gene which plays an important role in the production of L-glutamic acid in Coryneform bacteria which are used for the production of L-glutamic acid by fermentation. When this gene is amplified in L-lysine-producing Coryneform bacteria, the L-lysine productivity is improved. When this gene is disrupted in L-glutamic acid-producing Coryneform bacteria, the L-glutamic acid productivity is improved.

What is claimed is:

1. A biologically pure culture of an L-glutamic acid-producing Coryneform bacterium having substitution, deletion, insertion, addition or inversion of one or more nucleotides in a nucleotide sequence of a gene encoding an amino acid sequence comprising amino acid residues 37 to 543 of SEQ ID NO: 2, or a promoter thereof, on a chromosome, so that a protein having an activity to impart surfactant resistance to Coryneform bacteria does not normally function.

2. An isolated DNA fragment obtained from the genome of a Coryneform bacterium and encoding a protein comprising an amino acid sequence which comprises amino acid residues 37 to 543 of the sequence of SEQ ID NO: 2, said protein imparting surfactant resistance to the Coryneform bacterium when the protein is expressed in the Coryneform bacterium.

3. The isolated DNA of claim 2, which comprises nucleotides 467 to 1987 in the sequence of SEQ ID NO: 1.

4. A recombinant DNA containing the DNA of claim 2.

5. A Coryneform bacterium transformed with the recombinant DNA of claim 4.

6. A method for producing L-lysine, comprising cultivating the Coryneform bacterium of claim 5 in a liquid culture medium to produce L-lysine in the culture medium, followed by isolating the L-lysine.

7. An isolated DNA encoding a protein which is a mutant of an amino acid sequence comprising amino acid residues 37 to 543 of the sequence of SEQ ID NO: 2, wherein at least one amino acid residue in the sequence is substituted or deleted, or at least one amino acid residue is inserted between two adjacent amino acid residues in the sequence, or at least one amino acid residue is added to the sequence; and the protein imparts surfactant resistance to a Coryneform bacterium when the protein is expressed in the Coryneform bacterium.

8. The isolated DNA of claim 7, wherein the amino acid sequence comprising amino acid residues 37 to 543 of the sequence of SEQ ID NO: 2 is encoded by nucleotides 467 to 1987 in the sequence of SEQ ID NO: 1.

9. A recombinant DNA containing the DNA of claim 7.

10. A Coryneform bacterium transformed with the recombinant DNA of claim 9.

11. A method for producing L-lysine, comprising cultivating the Coryneform bacterium of claim 10 in a liquid culture medium to produce L-lysine in the culture medium, followed by isolating the L-lysine.

12. An isolated DNA encoding a protein which is a mutant of an amino acid sequence corresponding to amino acid residues 37 to 543 of the sequence of SEQ ID NO: 2, wherein at least one amino acid residue in the sequence is substituted or deleted, or at least one amino acid is inserted between two adjacent amino acid residues in the sequence;

the protein does not impart surfactant resistance to a Coryneform bacterium when the protein is expressed in the Coryneform bacterium; and said DNA can substitute for a DNA encoding an amino acid sequence comprising amino acid residues 37 to 543 of SEQ ID NO: 2, on a chromosome of a Coryneform bacterium, by homologous recombination.

13. The isolated DNA of claim 12, comprising a mutant of the nucleotide sequence of SEQ ID NO: 1 in which at least nucleotides 766 to 1366 of SEQ ID NO: 1 are deleted.

14. The isolated DNA of claim 12, comprising a mutant of the nucleotide sequence of SEQ ID NO: 1 in which nucleotides 766 to 1366 of SEQ ID NO: 1 are deleted.

15. A recombinant DNA containing the DNA of claim 12.

16. A Coryneform bacterium transformed with the recombinant DNA of claim 15.

17. A method for producing L-glutamic acid, comprising cultivating the Coryneform bacterium of claim 16 in a liquid culture medium to produce L-glutamic acid in the culture medium, followed by isolating the L-glutamic acid.

* * * * *

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
            (A) LENGTH: 2855 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 359..1987

(xi) SEQUENCE DESCRIPTION: SEQ ID NO:1:

GATCTTGGAA CTCGACAGTT TTCACCGTCC AGTTTGGAGC GCCTGAGCTT GCAAGCTCCA        60

GCAAGTCAGC ATTAGTGGAG CCTGTCACTT TTTCGTAAAT GACCTGGCCA AAGTCACCGT       120

TTTGGAGCAA TTTTTCCTTC AGGAGCTCAA CGTTTAGCGG CTCTCTGGAT CGTGAAATGT       180

CAACGTTCAT GGAAGCCAAT GTAGTGGGGT CGCGTCGAAA AGCGCGCTTT AAGGGCGACA       240

CGCCCAAAAA GTTTTACCTT TAAAAACTAC CCGCACGCAG CACGAACCTG TTCAGTGATG       300
```

-continued

| | |
|---|---:|
| TAAATCACCG CGGAAATATT GTGGACGTTA CCCCCGCCTA CCGCTACGAT TTCAAAAC | 358 |

```
ATG ACC ATT TCC TCA CCT TTG ATT GAC GTC GCC AAC CTT CCA GAC ATC       406
Met Thr Ile Ser Ser Pro Leu Ile Asp Val Ala Asn Leu Pro Asp Ile
 1               5                  10                 15

AAC ACC ACT GCC GGC AAG ATC GCC GAC CTT AAG GCT CGC CGC GCG GAA       454
Asn Thr Thr Ala Gly Lys Ile Ala Asp Leu Lys Ala Arg Arg Ala Glu
                 20                 25                 30

GCC CAT TTC CCC ATG GGT GAA AAG GCA GTA GAG AAG GTC CAC GCT GCT       502
Ala His Phe Pro Met Gly Glu Lys Ala Val Glu Lys Val His Ala Ala
             35                 40                 45

GGA CGC CTC ACT GCC CGT GAG CGC TTG GAT TAC TTA CTC GAT GAG GGC       550
Gly Arg Leu Thr Ala Arg Glu Arg Leu Asp Tyr Leu Leu Asp Glu Gly
     50                 55                 60

TCC TTC ATC GAG ACC GAT CAG CTG GCT CGC CAC CGC ACC ACC GCT TTC       598
Ser Phe Ile Glu Thr Asp Gln Leu Ala Arg His Arg Thr Thr Ala Phe
 65                 70                 75                 80

GGC CTG GGC GCT AAG CGT CCT GCA ACC GAC GGC ATC GTG ACC GGC TGG       646
Gly Leu Gly Ala Lys Arg Pro Ala Thr Asp Gly Ile Val Thr Gly Trp
                 85                 90                 95

GGC ACC ATT GAT GGA CGC GAA GTC TGC ATC TTC TCG CAG GAC GGC ACC       694
Gly Thr Ile Asp Gly Arg Glu Val Cys Ile Phe Ser Gln Asp Gly Thr
            100                105                110

GTA TTC GGT GGC GCG CTT GGT GAG GTG TAC GGC GAA AAG ATG ATC AAG       742
Val Phe Gly Gly Ala Leu Gly Glu Val Tyr Gly Glu Lys Met Ile Lys
        115                120                125

ATC ATG GAG CTG GCA ATC GAC ACC GGC CGC CCA TTG ATC GGT CTT TAC       790
Ile Met Glu Leu Ala Ile Asp Thr Gly Arg Pro Leu Ile Gly Leu Tyr
130                135                140

GAA GGC GCT GGC GCT CGC ATT CAG GAC GGC GCT GTC TCC CTG GAC TTC       838
Glu Gly Ala Gly Ala Arg Ile Gln Asp Gly Ala Val Ser Leu Asp Phe
145                150                155                160

ATT TCC CAG ACC TTC TAC CAA AAC ATT CAG GCT TCT GGC GTT ATC CCA       886
Ile Ser Gln Thr Phe Tyr Gln Asn Ile Gln Ala Ser Gly Val Ile Pro
                165                170                175

CAG ATC TCC GTC ATC ATG GGC GCA TGT GCA GGT GGC AAC GCT TAC GGC       934
Gln Ile Ser Val Ile Met Gly Ala Cys Ala Gly Gly Asn Ala Tyr Gly
            180                185                190

CCA GCC CTG ACC GAC TTC GTG GTC ATG GTG GAC AAG ACC TCC AAG ATG       982
Pro Ala Leu Thr Asp Phe Val Val Met Val Asp Lys Thr Ser Lys Met
        195                200                205

TTC GTT ACC GGC CCA GAC GTG ATC AAG ACC GTC ACC GGC GAG GAA ATC      1030
Phe Val Thr Gly Pro Asp Val Ile Lys Thr Val Thr Gly Glu Glu Ile
    210                215                220

ACC CAG GAA GAG CTT GGC GGA GCA ACC ACC CAC ATG GTG ACC GCT GGC      1078
Thr Gln Glu Glu Leu Gly Gly Ala Thr Thr His Met Val Thr Ala Gly
225                230                235                240

AAC TCC CAC TAC ACC GCT GCG ACC GAT GAG GAA GCA CTG GAT TGG GTA      1126
Asn Ser His Tyr Thr Ala Ala Thr Asp Glu Glu Ala Leu Asp Trp Val
                245                250                255

CAG GAC CTG GTG TCC TTC CTC CCA TCC AAC AAT CGC TCT TAC ACA CCA      1174
Gln Asp Leu Val Ser Phe Leu Pro Ser Asn Asn Arg Ser Tyr Thr Pro
            260                265                270

CTG GAA GAC TTC GAC GAG GAA GAA GGC GGC GTT GAA GAA AAC ATC ACC      1222
Leu Glu Asp Phe Asp Glu Glu Glu Gly Gly Val Glu Glu Asn Ile Thr
        275                280                285

GCT GAC GAT CTG AAG CTC GAC GAG ATC ATC CCA GAT TCC GCG ACC GTT      1270
Ala Asp Asp Leu Lys Leu Asp Glu Ile Ile Pro Asp Ser Ala Thr Val
    290                295                300

CCT TAC GAC GTC CGC GAT GTC ATC GAA TGC CTC ACC GAC GAT GGC GAA      1318
Pro Tyr Asp Val Arg Asp Val Ile Glu Cys Leu Thr Asp Asp Gly Glu
```

-continued

```
                305                 310                 315                 320
TAC CTG GAA ATC CAG GCA GAC CGC GCA GAA AAC GTT GTT ATT GCA TTC        1366
Tyr Leu Glu Ile Gln Ala Asp Arg Ala Glu Asn Val Val Ile Ala Phe
                    325                 330                 335

GGC CGC ATC GAA GGC CAG TCC GTT GGA TTT GTT GCC AAC CAG CCA ACC        1414
Gly Arg Ile Glu Gly Gln Ser Val Gly Phe Val Ala Asn Gln Pro Thr
                340                 345                 350

CAG TTC GCT GGC TGC CTG GAC ATC GAC TCC TCT GAG AAG GCA GCT CGC        1462
Gln Phe Ala Gly Cys Leu Asp Ile Asp Ser Ser Glu Lys Ala Ala Arg
            355                 360                 365

TTC GTC CGC ACC TGC GAC GCG TTT AAC ATC CCA ATC GTC ATG CTT GTC        1510
Phe Val Arg Thr Cys Asp Ala Phe Asn Ile Pro Ile Val Met Leu Val
        370                 375                 380

GAC GTC CCC GGC TTC CTT CCA GGC GCA GGC CAG GAG TAT GGT GGC ATC        1558
Asp Val Pro Gly Phe Leu Pro Gly Ala Gly Gln Glu Tyr Gly Gly Ile
385                 390                 395                 400

CTG CGT CGT GGC GCA AAG CTG CTC TAC GCA TAC GGC GAA GCA ACC GTT        1606
Leu Arg Arg Gly Ala Lys Leu Leu Tyr Ala Tyr Gly Glu Ala Thr Val
                405                 410                 415

CCA AAG ATT ACC GTC ACC ATG CGT AAG GCT TAC GGC GGA GCG TAC TGC        1654
Pro Lys Ile Thr Val Thr Met Arg Lys Ala Tyr Gly Gly Ala Tyr Cys
                    420                 425                 430

GTG ATG GGT TCC AAG GGC TTG GGC TCT GAC ATC AAC CTT GCA TGG CCA        1702
Val Met Gly Ser Lys Gly Leu Gly Ser Asp Ile Asn Leu Ala Trp Pro
                435                 440                 445

ACC GCA CAG ATC GCC GTC ATG GGC GCT GCT GGC GCA GTC GGA TTC ATC        1750
Thr Ala Gln Ile Ala Val Met Gly Ala Ala Gly Ala Val Gly Phe Ile
            450                 455                 460

TAC CGC AAG GAG CTC ATG GCA GCT GAT GCC AAG GGC CTC GAT ACC GTA        1798
Tyr Arg Lys Glu Leu Met Ala Ala Asp Ala Lys Gly Leu Asp Thr Val
465                 470                 475                 480

GCT CTG GCT AAG TCC TTC GAG CGC GAG TAC GAA GAC CAC ATG CTC AAC        1846
Ala Leu Ala Lys Ser Phe Glu Arg Glu Tyr Glu Asp His Met Leu Asn
                485                 490                 495

CCG TAC CAC GCT GCA GAA CGT GGC CTG ATC GAC GCC GTG ATC CTG CCA        1894
Pro Tyr His Ala Ala Glu Arg Gly Leu Ile Asp Ala Val Ile Leu Pro
                    500                 505                 510

AGC GAA ACC CGC GGA CAG ATT TCC CGC AAC CTT CGC CTG CTC AAG CAC        1942
Ser Glu Thr Arg Gly Gln Ile Ser Arg Asn Leu Arg Leu Leu Lys His
                515                 520                 525

AAG AAC GTC ACT CGC CCT GCT CGC AAG CAC GGC AAC ATG CCA CTG            1987
Lys Asn Val Thr Arg Pro Ala Arg Lys His Gly Asn Met Pro Leu
            530                 535                 540

TAAATCGGCG AATCCATAAA GGTTCAAAAG AATTCAATAA GGATTCGATA AGGGTTCGAT      2047
AAGGGTTCGA TAAGGGCCGA CTTAAATGAT TGGATGTAAA GAAATACCAA TGAAAATTGG      2107
CAACTCTTTA CACCCAATCT TTAAGACATG GGGGGTGGCG CTGGGCTAAT ATAACCGGTT      2167
AGCGAAACGA TTAGTCCCTT GTTAGGGGGA TTAACCCTCG AAGTGGGTCG TATTTTGGCG      2227
TTTGTATGTT CACACAAGAA CCCTGCACAA CGCCTTCAAA GTACGTCGAC CACGACCAAG      2287
CGCATTATTC ACTCTCACCC TTCAGGATTT AGACTAAGAA ACCATGACTG CAGCACAGAC      2347
CAAACCTGAC CTCACCACCA CGGCTGGAAA GCTGTCCGAT CTTCGCTCCC GTCTTGCAGA      2407
AGCTCAAGCT CCAATGGGCG AAGCAACTGT AGAAAAGTG CACGCTGCTG GCAGGAAGAC       2467
TGCCCGCGAA CGTATCGAGT ATTTGCTCGA TGAGGGCTCT TTCGTAGAGA TCGATGCTCT      2527
TGCTCGTCAC CGTTCCAAGA ACTTCGGCCT GGATGCCAAG CGTCCAGCTA CTGACGGTGT      2587
TGTGACTGGT TACGGCACCA TCGATGGCCG TAAGGTCTGT GTGTTCTCCC AGGACGGCGC      2647
```

```
TGTATTCGGT GGCGCTTTGG GTGAAGTTTA TGGTGAAAAG ATCGTTAAGG TTATGGATCT      2707

TGCGATCAAG ACCGGTGTGC CTTTGATCGG AATCAATGAG GGTGCTGGTG CGCGTATCCA      2767

GGAAGGTGTT GTGTCTCTGG GTCTGTACTC ACAGATTTTC TACCGCAACA CCCAGGCGTC      2827

TGGCGTTATC CCACAGATCT CTTTGATC                                         2855
```

(2) INFORMATION FOR SEQ ID NO:2:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Ile Ser Ser Pro Leu Ile Asp Val Ala Asn Leu Pro Asp Ile
 1               5                  10                  15

Asn Thr Thr Ala Gly Lys Ile Ala Asp Leu Lys Ala Arg Arg Ala Glu
                20                  25                  30

Ala His Phe Pro Met Gly Glu Lys Ala Val Glu Lys Val His Ala Ala
            35                  40                  45

Gly Arg Leu Thr Ala Arg Glu Arg Leu Asp Tyr Leu Leu Asp Glu Gly
    50                  55                  60

Ser Phe Ile Glu Thr Asp Gln Leu Ala Arg His Arg Thr Thr Ala Phe
65                  70                  75                  80

Gly Leu Gly Ala Lys Arg Pro Ala Thr Asp Gly Ile Val Thr Gly Trp
                85                  90                  95

Gly Thr Ile Asp Gly Arg Glu Val Cys Ile Phe Ser Gln Asp Gly Thr
            100                 105                 110

Val Phe Gly Gly Ala Leu Gly Glu Val Tyr Gly Glu Lys Met Ile Lys
    115                 120                 125

Ile Met Glu Leu Ala Ile Asp Thr Gly Arg Pro Leu Ile Gly Leu Tyr
130                 135                 140

Glu Gly Ala Gly Ala Arg Ile Gln Asp Gly Ala Val Ser Leu Asp Phe
145                 150                 155                 160

Ile Ser Gln Thr Phe Tyr Gln Asn Ile Gln Ala Ser Gly Val Ile Pro
                165                 170                 175

Gln Ile Ser Val Ile Met Gly Ala Cys Ala Gly Gly Asn Ala Tyr Gly
            180                 185                 190

Pro Ala Leu Thr Asp Phe Val Val Met Val Asp Lys Thr Ser Lys Met
    195                 200                 205

Phe Val Thr Gly Pro Asp Val Ile Lys Thr Val Thr Gly Glu Glu Ile
210                 215                 220

Thr Gln Glu Glu Leu Gly Gly Ala Thr Thr His Met Val Thr Ala Gly
225                 230                 235                 240

Asn Ser His Tyr Thr Ala Ala Thr Asp Glu Glu Ala Leu Asp Trp Val
                245                 250                 255

Gln Asp Leu Val Ser Phe Leu Pro Ser Asn Asn Arg Ser Tyr Thr Pro
            260                 265                 270

Leu Glu Asp Phe Asp Glu Glu Glu Gly Gly Val Glu Glu Asn Ile Thr
    275                 280                 285

Ala Asp Asp Leu Lys Leu Asp Glu Ile Ile Pro Asp Ser Ala Thr Val
290                 295                 300

Pro Tyr Asp Val Arg Asp Val Ile Glu Cys Leu Thr Asp Asp Gly Glu
305                 310                 315                 320
```

```
Tyr Leu Glu Ile Gln Ala Asp Arg Ala Glu Asn Val Val Ile Ala Phe
            325                 330                 335

Gly Arg Ile Glu Gly Gln Ser Val Gly Phe Val Ala Asn Gln Pro Thr
            340                 345                 350

Gln Phe Ala Gly Cys Leu Asp Ile Asp Ser Ser Glu Lys Ala Ala Arg
        355                 360                 365

Phe Val Arg Thr Cys Asp Ala Phe Asn Ile Pro Ile Val Met Leu Val
    370                 375                 380

Asp Val Pro Gly Phe Leu Pro Gly Ala Gly Gln Glu Tyr Gly Gly Ile
385                 390                 395                 400

Leu Arg Arg Gly Ala Lys Leu Leu Tyr Ala Tyr Gly Glu Ala Thr Val
                405                 410                 415

Pro Lys Ile Thr Val Thr Met Arg Lys Ala Tyr Gly Gly Ala Tyr Cys
            420                 425                 430

Val Met Gly Ser Lys Gly Leu Gly Ser Asp Ile Asn Leu Ala Trp Pro
        435                 440                 445

Thr Ala Gln Ile Ala Val Met Gly Ala Ala Gly Ala Val Gly Phe Ile
    450                 455                 460

Tyr Arg Lys Glu Leu Met Ala Ala Asp Ala Lys Gly Leu Asp Thr Val
465                 470                 475                 480

Ala Leu Ala Lys Ser Phe Glu Arg Glu Tyr Glu Asp His Met Leu Asn
                485                 490                 495

Pro Tyr His Ala Ala Glu Arg Gly Leu Ile Asp Ala Val Ile Leu Pro
            500                 505                 510

Ser Glu Thr Arg Gly Gln Ile Ser Arg Asn Leu Arg Leu Leu Lys His
        515                 520                 525

Lys Asn Val Thr Arg Pro Ala Arg Lys His Gly Asn Met Pro Leu
530                 535                 540
```